US011013810B2

(12) United States Patent
Li et al.

(10) Patent No.: US 11,013,810 B2
(45) Date of Patent: *May 25, 2021

(54) PHARMACEUTICAL COMPOSITION AND METHODS OF USES

(71) Applicant: Foresee Pharmaceuticals Co., Ltd., Taipei (TW)

(72) Inventors: Yuhua Li, Landenberg, PA (US); ChiaTing Huang, New Taipei (TW); John Mao, San Bruno, CA (US)

(73) Assignee: Foresee Pharmaceuticals Co., Ltd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/739,359

(22) Filed: Jan. 10, 2020

(65) Prior Publication Data
US 2020/0147226 A1    May 14, 2020

Related U.S. Application Data

(63) Continuation of application No. 15/680,946, filed on Aug. 18, 2017, now Pat. No. 10,532,102.

(60) Provisional application No. 62/377,427, filed on Aug. 19, 2016.

(51) Int. Cl.
| | | |
|---|---|---|
| A61K 47/40 | (2006.01) | |
| A61K 9/00 | (2006.01) | |
| A61K 47/18 | (2017.01) | |
| A61K 31/4178 | (2006.01) | |
| A61K 9/48 | (2006.01) | |
| A61K 9/16 | (2006.01) | |
| A61K 9/10 | (2006.01) | |

(52) U.S. Cl.
CPC ............ *A61K 47/40* (2013.01); *A61K 9/0053* (2013.01); *A61K 9/10* (2013.01); *A61K 9/1652* (2013.01); *A61K 9/48* (2013.01); *A61K 31/4178* (2013.01); *A61K 47/183* (2013.01)

(58) Field of Classification Search
CPC ... A61K 9/00; A61K 9/10; A61K 9/16; A61K 9/48; A61K 31/4178; A61K 47/18; A61K 47/40

See application file for complete search history.

(56) References Cited

U.S. PATENT DOCUMENTS

| | | | |
|---|---|---|---|
| 4,352,793 A | 10/1982 | Yamahira et al. | |
| 4,352,794 A | 10/1982 | Koch | |
| 4,568,507 A | 2/1986 | Baxter | |
| 4,727,064 A | 2/1988 | Pitha | |
| 4,994,273 A | 2/1991 | Zentner et al. | |
| 5,134,127 A | 7/1992 | Stella et al. | |
| 5,324,750 A | 6/1994 | Lincoln et al. | |
| 7,179,831 B2 | 2/2007 | Yang | |
| 10,532,102 B2* | 1/2020 | Li  ................ | A61K 9/1652 |
| 10,851,089 B2* | 12/2020 | Yang  ................ | C07D 407/14 |
| 2006/0041000 A1* | 2/2006 | Yang  ................ | A61P 35/00 |
| | | | 514/389 |
| 2007/0270379 A1 | 11/2007 | Freiss et al. | |
| 2014/0371283 A1 | 12/2014 | John et al. | |
| 2015/0025023 A1 | 1/2015 | Savage et al. | |

FOREIGN PATENT DOCUMENTS

| | | |
|---|---|---|
| CN | 1706501 A | 12/2005 |
| EP | 0449167 A1 | 10/1991 |
| EP | 0524632 A1 | 1/1993 |
| EP | 0991407 A2 | 4/2000 |
| EP | 1018340 A1 | 7/2000 |
| WO | 97018245 A1 | 5/1997 |
| WO | 97018839 A1 | 5/1997 |
| WO | 2004096284 A1 | 11/2004 |
| WO | 2010126818 A1 | 11/2010 |
| WO | 2011103150 A2 | 8/2011 |
| WO | 2014161131 A1 | 10/2014 |
| WO | 2017067980 A1 | 4/2017 |

OTHER PUBLICATIONS

Morin-Crini (Progress in Polymer Science vol. 38 pages 344-368. Published 2013) (Year: 2013).*
Han (Advances in Characterization of Pharmaceutical Hydrates. Trends in Bio/Pharmaceutical Industry, pp. 25-29. Mar. 2006 (Year: 2006).*
Vippagunta et al (Adv Drug Deliv Rev 48:3-26, 2001) (Year: 2001).*
Patil et al., "Effect of L-Arginine on Bicalutamide Complexation with Hydroxypropyl-Beta-Cyclodextrin", Digest Journel of Nanomaterials and Biostructures, vol. 3, No. 2, pp. 89-98, 2008.
Int'l Search Report and Written Opinion dated Oct. 30, 2017 in Int'l Application No. PCT/US2017/047609.
Tambosi et al., "Challenges to Improve the Biopharmaceutical Properites of Poorly Water-Soluble Drugs and the Application of the Solid Dispersion technology" Revista Materia, vol. 23, No. 04, 13 pages, 2018.
Banchero et al. Characterization of Ketoprofen/Methyl-β-Cyclodextrin Complexes Prepared Using Supercritical Carbon Dioxide. Journal of Chemistry, vol. 2013, Article ID 583952, 8 pages.

(Continued)

*Primary Examiner* — Theodore R. Howell
*Assistant Examiner* — George W Kosturko
(74) *Attorney, Agent, or Firm* — Ice Miller LLP

(57) ABSTRACT

The present invention provides compositions or formulations comprising the combination of a compound of 5-[3-(4-benzyloxyphenylthio)-fur-2-yl]-imidazolidin-2,4-dione or a salt thereof or hydrate of the foregoing, and a cyclodextrin; or in further combination with an excipient comprising L-Arginine or other additives, wherein the compositions or formulations increases water solubility and oral bioavailability of 5-[3-(4-benzyloxyphenylthio)-fur-2-yl]-imidazolidin-2,4-dione and its related compounds. The method of making or using the compositions or formulations is also disclosed. Such compositions or formulations may be used in treatment of certain diseases including asthma through inhibition of matrix metalloproteinase-12.

21 Claims, 5 Drawing Sheets

(56) References Cited

OTHER PUBLICATIONS

Del Valle, "Cyclodextrins and Their uses: a Review", Process Biochemistry, 39, pp. 1033-1046, 2004.
Teja et al., "Drug-excipient behavior in polymeric amorphous solid dispersions", J. Excipients and Food Chem, 4(3), 2013.
Freitas et al. Inclusion complex of methyl-cyclodextrin and olanzapine as potential drug delivery system for schizophrenia. Carbohydrate Polymers 89 (2012) 1095-1100.
Zaibunnisa et al., "Characterisation and Solubility Study of g-cyclodextrin and b-carotene complex" International Food Research Journal 18 (3), pp. 1061-1065, 2011.
International Preliminary Report on Patentability dated Feb. 19, 2019 in International Application No. PCT/US2017/047609.
Blitz et al., "Review: The Preparation of Hydantoins," Communication from the Institute of Chemistry at the University of Wroclaw, pp. 1-34 (1926) (English Translation dated Apr. 25, 2014).
Jansen, et al., "Some physical-chemical properties of dantrolene and two of its analogues,"International Journal of Pharmaceutics, vol. 75, pp. 193-199, (1991).
Savolainen, et al., "Improved dissolution and bioavailability of phenytoin by sulfobutylether-P-cyclodextrin ((SBE) 7m-P-CD) and hydroxypropyl-P-cyclodextrin (HP-P-CD) complexation", International Journal of Pharmaceutics, vol. 165, pp. 69-78, (1998).
Office Action dated Oct. 31, 2019 in RU Application No. 2019107579.

* cited by examiner

PHARMACEUTICAL COMPOSITION AND METHODS OF USES

CROSS-REFERENCE TO RELATED APPLICATION

This application is a continuation application claiming priority under 35 U.S.C. § 120 to U.S. patent application Ser. No. 15/680,946 filed Aug. 18, 2017, which claims priority to U.S. Provisional Patent Application No. 62/377,427, filed on Aug. 19, 2016, the disclosure of each of which is hereby incorporated into this application by reference in its entirety.

FIELD OF THE INVENTION

The present invention relates to compositions of combination of 5-[3-(4-benzyloxyphenylthio)-fur-2-yl]-imidazolidin-2,4-dione or its analogues with a cyclodextrin, and methods of use thereof. The compositions of 5-[3-(4-benzyloxyphenylthio)-fur-2-yl]-imidazolidin-2,4-dione or its analogues with a cyclodextrin increase water solubility of 5-[3-(4-benzyloxyphenylthio)-fur-2-yl]-imidazolidin-2,4-dione or its analogues thereby enhance the oral bioavailability. Moreover, the present invention relates to the use of pharmaceutical compositions comprising 5-[3-(4-benzyloxyphenylthio)-fur-2-yl]-imidazolidin-2,4-dione or its analogues with a cyclodextrin in the treatment of a disease or condition that is or is believed to be responsive to inhibition of matrix metalloproteinase-12.

BACKGROUND OF THE INVENTION

A series of compounds of 5-[3-(4-benzyloxyphenylthio)-fur-2-yl]-imidazolidin-2,4-dione or its analogues were disclosed in United States Patent Application 20060041000. These compounds were designed to be used as inhibitors of macrophage elastase. All these compounds are hydantoin derivatives and tested in vitro for their use as matrix metalloproteinase (MMP) inhibitors.

As shown in the United States Patent Application 20060041000, all compounds tested show desirable activity and favorable selectivity profile. IC50s on MMP-12 fall in the range of 1-300 nM, therefore they are all considered to be active. Most of the above compounds do not show inhibition on MMP-1 and MMP-7 at 10 uM. Their selectivity for MMP-12 over MMP-2, MMP-3, MMP-9 and MMP-13 range from 50 to 1000 fold. These compounds seem to possess some potentials to be used in the treatment of diseases or conditions mediated by MMP-12, such as asthma, chronic obstructive pulmonary diseases (COPD), arthritis, cancer, heart disease and nephritis. However, except for the IC50 data for limited MMPs, there were no further biological data provided in detail. In addition, except the NMR and MS data, no other physical and chemical property data were provided.

Therefore, it would be desirable to understand the characteristics of these compounds and develop suitable formulations to use 5-[3-(4-benzyloxyphenylthio)-fur-2-yl]-imidazolidin-2,4-dione or its analogues for potential treatment of various diseases through inhibition of MMP.

According to the teaching of the United States Patent Application 20060041000, MMP Inhibitory Assays were conducted in aqueous buffer (50 mM Hepes, 10 mM CaCl2, 0.05% Brij 35, pH 7.5), indicating that these compounds should be fairly water soluble. However, it was unexpectedly discovered that these compounds have very low aqueous solubility. 5-[3-(4-benzyloxyphenylthio)-fur-2-yl]-imidazolidin-2,4-dione and its analogues not only exhibit a low solubility in water, but also in an acidic environment. Consequently, when administered orally in a conventional solid dosage form, a low bioavailability may be expected.

Therefore, there remains a need for developing formulations of these compounds, such as formulations that render these compounds suitable for non-invasive such as oral, intranasal and/or sublingual administrations.

SUMMARY OF THE INVENTION

The present invention provides compositions or formulations comprising the combination of a compound of the formula (I) or a salt thereof or hydrate of the foregoing and a cyclodextrin.

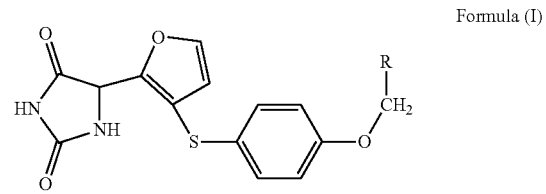

Formula (I)

Also provided are methods of producing compositions containing a compound of the formula (I) or a salt thereof and methods of treating a disease or indication that is responsive to a compound of the formula (I) or a salt thereof comprising administering a pharmaceutical composition containing a compound of the formula (I) or a salt thereof to an animal or human subject.

One object of the present invention is to increase the water-solubility of compound of the formula (I). The present invention thus relates to methods for improving the solubility of compound of the formula (I), said method comprising a pharmaceutical composition comprising the combination of a compound of the formula (I) and a cyclodextrin.

DETAILED DESCRIPTION OF THE INVENTION

Figure 1:
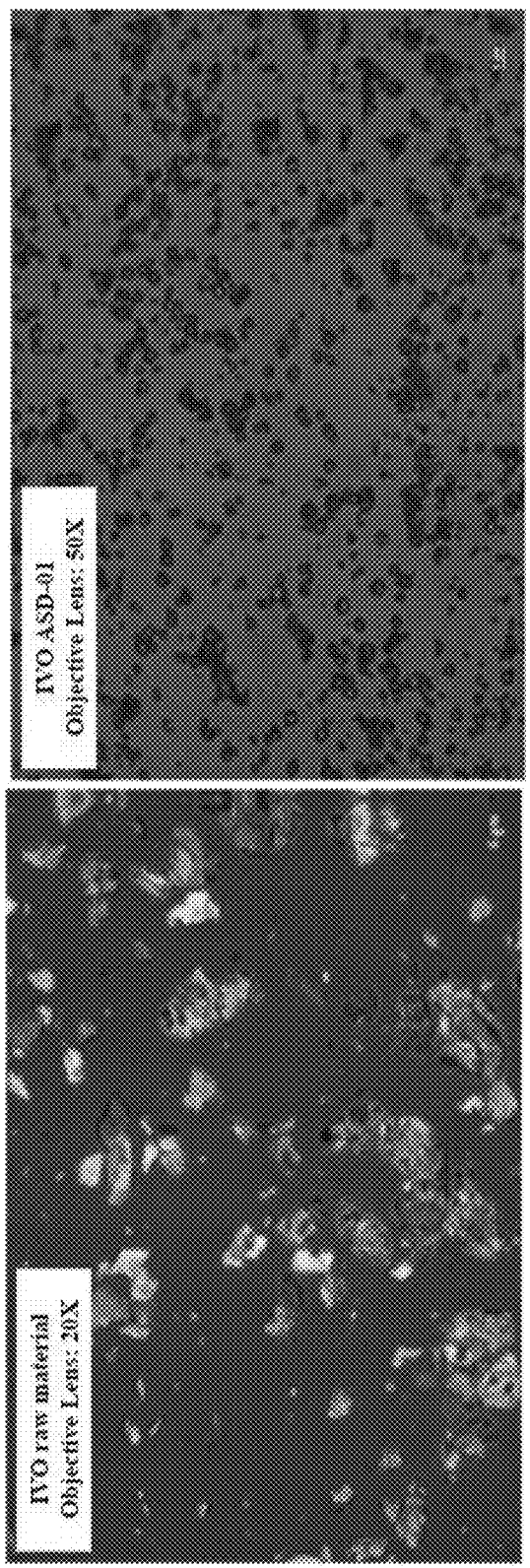
FIG. 1 Polarized Light Microscopy (PLM) results of raw materials and the prepared complex of compound IVO: HPBCD (1:3, w/w) by spray drying method.

The present invention provides a composition comprising a compound of the formula (I) and a cyclodextrin. The composition significantly increases the solubility of the compound of the formula (I) in water.

According to the present invention, the compound of the formula (I), wherein R is selected from the group consisting of phenyl, 4-benzyloxyphenyl, 4-biphenyl, 4-methoxyphenyl, 3-methoxyphenyl, 2-methoxyphenyl, 3,5-dimethoxyphenyl, 4-chlorophenyl, 3-chlorophenyl, 2-chlorophenyl, 4-methylphenyl, 3-methylphenyl, 2-methylphenyl, and 3-trifluoromethylphenyl.

It is understood that the salts, such as pharmaceutically acceptable salts, and solvates thereof, are also intended by the descriptions provided herein. Thus, all salt and non-salt forms of the compound of the formula (I) and solvates of the foregoing are embraced by the invention and descriptions of the compound of the formula (I) provided herein.

According to the present invention, the cyclodextrin for use in the compositions herein is a water soluble unsubstituted or substituted alpha-cyclodextrin (ACD), beta-cyclodextrin (BCD), or gamma-cyclodextrin (GCD). In some embodiments, the beta-cyclodextrin is selected from the group consisting of methyl beta-cyclodextrin (MBCD), hydroxypropyl beta-cyclodextrin (HPBCD), and sulfobutylether beta-cyclodextrin (SBEBCD). In some embodiments, the beta-cyclodextrin is methyl beta-cyclodextrin or hydroxypropyl beta-cyclodextrin. In some embodiments, the gamma-cyclodextrin is hydroxypropyl gamma-cyclodextrin (HPGCD). In one preferred embodiment, the cyclodextrin is hydroxypropyl beta-cyclodextrin (HPBCD) or methyl beta-cyclodextrin (MBCD).

According to the present invention, methods for improving the solubility of a compound of the formula (I) in water comprising combining the compound of the formula (I) with a cyclodextrin are provided. In one embodiment, a method of increasing the water solubility of a compound of formula (I) is provided, wherein the method comprises forming an inclusion complex of a compound of the formula (I) and a cyclodextrin. In some embodiments, the solubility of the compound of the formula (I), when present as an inclusion complex with a cyclodextrin in deionized water at room temperature, is increased by at least 2-fold, when compared to the solubility of the compound of formula (I) in an uncomplexed form under the same conditions. The term "room temperature" as defined herein is about 20 to 25 degrees Celsius with an average of 23° C. In other embodiments, the solubility, such as the aqueous solubility, of the compound of the formula (I) in a composition increases by at least 5-fold to 2,000-fold or more over compound of the formula (I) alone. Solubility comparisons may be assessed by methods known to one skilled in the art, such as any of the specific methods and conditions detailed herein.

According to the present invention, the oral bioavailability of the compound of the formula (I), when present with a cyclodextrin, is at least 50% greater than the oral bioavailability of the compound of the formula (I) in absence of a cyclodextrin. Oral bioavailability, and comparisons thereof, may be assessed by methods known in the art, including any of the specific methods described herein.

According to the present invention, a composition of a compound of formula (I) and a cyclodextrin is provided, wherein the composition induces a greater maximum concentration (Cmax) of the compound systemically than what is achievable when the compound is administered alone in the same amount and under the same conditions. In one embodiment, a composition of the compound of formula (I) induces at least 1.5 or more times greater Cmax for the compound systemically than what is achievable when the compound is administered alone in the same amount and under the same conditions. In some embodiments, the Cmax of the compound of the formula (I), when administered to an animal or human with a cyclodextrin, is at least 2 times greater than the Cmax of the compound of the formula (I) administered alone under the same conditions.

According to the present invention, a composition of a compound of formula (I) and a cyclodextrin is provided, wherein the composition induces a greater area under the plasma concentration vs. time curve (AUC) of the compound than what is achievable when the compound is administered in the absence of a cyclodextrin in the same amount and under the same conditions. In one embodiment, a composition of the compound of formula (I) with a cyclodextrin induces at least 2 or more times greater AUC of compound than what is achievable when the compound is administered in the absence of a cyclodextrin in the same amount and under the same conditions. In some embodiments, the AUC of the compound of the formula (I), when administered to an animal with a cyclodextrin, is at least 2 times greater than the AUC of the compound of the formula (I) administered in the absence of a cyclodextrin in the same amount and under the same conditions.

According to the present invention, a composition of a compound of formula (I) and a cyclodextrin is provided, wherein the composition induces a change in the time to reach the maximum plasma level (Tmax) of the compound than what is achievable when the compound is administered in the absence of a cyclodextrin in the same amount and under the same conditions. In another embodiment, a composition of the compound of formula (I) with a cyclodextrin reduces the maximum plasma level (Tmax) of the compound by 1 or 2 fold over what is achievable when the compound is administered in the absence of the cyclodextrin in the same amount and under the same conditions. In some embodiments, the Tmax of the compound of the formula (I), when administered to an individual with a cyclodextrin, is at least 2 times shorter than that of the compound of the formula (I) administered in the absence of the cyclodextrin in the same amount and under the same conditions. In some embodiments, the compound of the formula (I) with a cyclodextrin reduces Tmax by at least any of 1, 2, and 3 hours or more.

According to the present invention, a composition comprising a compound of the formula (I) and a cyclodextrin is provided, wherein the molar ratio of the compound of formula (I) to the cyclodextrin is from 1:1 to 1:300, preferably from 1:1 to 1:50, and more preferably from 1:1 to 1:10. In one embodiment, the composition comprises a complex of a compound of the formula (I) and a cyclodextrin, wherein at least a moiety of compound of the formula (I) has inserted itself, at least partially, into the cavity of the cyclodextrin to form an inclusion complex. In another embodiment, the composition comprises a physical mixture of a cyclodextrin and a compound of the formula (I), wherein the physical mixture does not comprise or is substantially free of at least a moiety of compound of the formula (I) has inserted itself, at least partially, into the cavity of cyclodextrin. In another embodiment, a composition comprising a) a compound of the formula (I), or a salt thereof, or solvate of the foregoing; b) a cyclodextrin; and c) an additive, are provided. In one embodiment, the additive is a pharmaceutically acceptable excipient. In another embodiment, the additive will further increase the solubility of compound of the formula (I) in an aqueous solution. The additive may be in liquid, solid or semi-solid form. In some embodiments, the additive is selected from the group, but not limited to, consisting of citric acid, PEG-4000, PVP K40, PVP K10, NaCMC, L-Arginine, Lysine, and D-Mannitol. In one preferred embodiment, the additive is L-arginine and in another preferred embodiment, the additive is lysine.

Compositions comprising a compound of the formula (I) and a cyclodextrin may further comprise additional formulation components, also referred to herein as additional agents. In some embodiments of the formulations described herein, the formulation further comprises a carrier; in some other embodiments of the formulations described herein, the formulation further comprises an antioxidant.

According to the present invention, a composition comprising (a) a compound of the formula (I), or a salt thereof, or solvate of the foregoing; (b) a cyclodextrin; and (c) a carrier, is a solid formulation. In some embodiments, the formulation is a semi-solid. In some embodiments, the formulation is a liquid.

EXAMPLES

The following examples illustrate the compositions and methods of the present invention. The examples do not limit the invention, but are provided to teach how to make useful controlled release drug delivery compositions.

Example 1: Synthesis of the Compound of Formula (I)

The synthesis of compound of the formula (I), i.e., 5-[3-(4-benzyloxyphenylthio)-fur-2-yl]-imidazolidin-2,4-dione and its analogues were performed according to the method disclosed in United States Patent Application 20060041000. The following compounds were synthesized and characterized.

IVE: 5-{3-[4-(3-Methoxybenzyloxy) phenylthio]fur-2-yl}imidazolidine-2,4-dione
IVH: 5-{3-[4-(4-Chlorobenzyloxy) phenylthio]fur-2-yl}imidazolidine-2,4-dione
IVO: 5-{3-[4-(3-Methyl-benzyloxy) phenylthio]fur-2-yl}imidazolidine-2,4-dione
IVP: 5-{3-[4-(2-Methyl-benzyloxy) phenylthio]fur-2-yl}imidazolidine-2,4-dione
IVQ: 5-{3-[4-(3-Trifluoromethyl-benzyloxy) phenylthio]fur-2yl}imidazolidine-2,4-dione

Example 2: Effect of Different Cyclodextrins on the Aqueous Solubility of 5-{3-[4-(3-Methoxybenzyloxy) phenylthio]fur-2-yl}imidazolidine-2,4-dione (IVE)

Table 1 lists various commercially available cyclodextrins (CDs). In order to test the effect of various CDs on the aqueous solubility of compound IVE, 1 mL of each of the following aqueous solutions as described in Table 2 was prepared. Excess IVE was added to each of these solutions and the samples were shaken at room temperature for 24 hours on an orbital shaker at 200 rpm. Excess IVE was present in all samples at all times to obtain solubility. After 24-hours, the samples were centrifuged. An aliquot of the supernatant was diluted, if necessary, and assayed by HPLC. Table 2 shows that both ACD and HPGCD do not improve aqueous solubility of compound IVE significantly, while MBCD, SBEBCD, and HPBCD can significantly enhance the aqueous solubility of compound IVE. These results indicate that only beta cyclodextrins may improve the solubility of compound IVE. The size of the compound may allow it to form an inclusion complex, resulting in a higher aqueous solubility. The enhancement effect on the aqueous solubility of compound IVO is in the order of MBCD>SBEBCD>HPBCD>HPGCD>ACD. MBCD is the most effective solubility improving agent in this experiment.

TABLE 1

Commercially available cyclodextrins

| Cyclodextrin Type | Trade Name | Number of Glucopyranose Units | Abbreviation | Molecular Weight | Water Solubility (25° C.) (mg/mL) |
|---|---|---|---|---|---|
| Methyl beta-Cyclodextrin | CAVASOL ® W7 M Pharma | 7 | MBCD | 1310 | >750 |
| Hydroxypropyl beta-cyclodextrin | KLEPTOSE ® HPB Pharma | 7 | HPBCD | 1400 | >750 |
| Sulfobutyl-ether beta-cyclodextrin | Captisol ® | 7 | SBEBCD | 2163 | >500 |
| Hydroxypropyl gamma-cyclodextrin | CAVASOL ® W8 HP Pharma | 8 | HPGCD | 1574 | >750 |
| Alpha-cyclodextrin | CAVAMAX ® | 6 | ACD | 973 | 145 |

TABLE 2

Solubility of compound IVE in different CD's solution

| CD Concentration | Concentration of IVE (mg/mL) | | | | ACD Concentration | ACD |
|---|---|---|---|---|---|---|
| | HPBCD | MBCD | HPGCD | SBEBCD | | |
| 0 mg/ml | 0.023 | 0.023 | 0.023 | 0.023 | 0 mg/ml | 0.023 |
| 100 mg/ml | 0.744 | 3.251 | 0.059 | 0.815 | 40 mg/ml | 0.053 |

Example 3: Effect of Different Cyclodextrins on the Aqueous Solubility of 5-{3-[4-(2-Methyl-benzyloxy) phenylthio]fur-2-yl}imidazolidine-2,4-dione (IVP)

In order to test the effect of various CDs on the aqueous solubility of compound IVP, 1 mL of each of the following aqueous solutions as described in Table 3 was prepared. Excess IVP was added to each of these solutions and the samples were shaken at room temperature for 24 hours on an orbital shaker at 200 rpm. Excess IVP was present in all samples at all times. After 24-hours, the samples were centrifuged. An aliquot of the supernatant was diluted, if necessary, and assayed by HPLC. Table 3 shows that both ACD and HPGCD do not improve aqueous solubility of compound IVP significantly, while MBCD, SBEBCD, and HPBCD can significantly enhance the aqueous solubility of compound IVP. These results indicate that only beta cyclodextrins may improve the solubility of compound IVP. The size of the compound may allow it to form an inclusion complex, resulting in a higher aqueous solubility. The enhancement effect on the aqueous solubility of compound IVP is in the order of MBCD>SBEBCD>HPBCD>HPGCD>ACD. MBCD is the most effective solubility improving agent in this experiment.

TABLE 3

Solubility of compound IVP in different CD's solution

| CD Concentration | Concentration of IVP (mg/mL) | | | | ACD Concentration | ACD |
|---|---|---|---|---|---|---|
| | HPBCD | MBCD | HPGCD | SBEBCD | | |
| 0 mg/ml | 0.064 | 0.064 | 0.064 | 0.064 | 0 mg/ml | 0.064 |
| 100 mg/ml | 0.727 | 6.269 | 0.001 | 0.805 | 40 mg/ml | 0.015 |

Example 4: Effect of Different Cyclodextrins on the Aqueous Solubility of 5-{3-[4-(3-Methyl-benzyloxy)phenylthio]-fur-2-yl}-imidazolidin-2,4-dione (IVO)

In order to test the effect of various CDs on the aqueous solubility of compound IVO, 1 mL of each of the following aqueous solutions as described in Table 4 was prepared. Excess IVO was added to each of these solutions and the samples were shaken at room temperature for 24 hours on an orbital shaker at 200 rpm. Excess IVO was present in all samples at all times. After 24-hours, the samples were centrifuged. An aliquot of the supernatant was diluted, if necessary, and assayed by HPLC. Table 4 shows that both ACD and HPGCD do not improve aqueous solubility of compound IVO, while MBCD, SBEBCD, and HPBCD can significantly enhance the aqueous solubility of compound IVO. These results indicate that only beta cyclodextrins may improve the solubility of compound IVO. The size of the compound may allow it to form an inclusion body complex, resulting in a higher aqueous solubility. The enhancement effect on the aqueous solubility of compound IVO is in the order of MBCD>SBEBCD>HPBCD>HPGCD>ACD. MBCD is the most effective solubility improving agent in this experiment.

TABLE 4

Solubility of compound IVO in different CD's solution

| CD Concentration | Concentration of compound IVO (mg/mL) | | | | ACD Concentration | ACD |
|---|---|---|---|---|---|---|
| | HPBCD | MBCD | HPGCD | SBEBCD | | |
| 0 mg/ml | 0.026 | 0.026 | 0.026 | 0.026 | 0 mg/ml | 0.026 |
| 25 mg/ml | 0.037 | 0.244 | 0.009 | 0.094 | 5 mg/ml | 0.037 |
| 50 mg/ml | 0.083 | 0.477 | 0.016 | 0.116 | 10 mg/ml | 0.030 |
| 75 mg/ml | 0.108 | 0.673 | 0.006 | 0.156 | 15 mg/ml | 0.026 |
| 100 mg/ml | 0.184 | 1.066 | 0.002 | 0.174 | 20 mg/ml | 0.013 |
| 150 mg/ml | 0.312 | 1.695 | 0.004 | 0.315 | 30 mg/ml | 0.010 |
| 200 mg/ml | 0.467 | 1.784 | 0.003 | 0.761 | 40 mg/ml | 0.017 |

Example 5: Effect of Different Cyclodextrins on the Aqueous Solubility of 5-{3-[4-(3-Trifluoromethyl-benzyloxy) phenylthio]fur-2y1}imidazolidine-2,4-dione (IVQ)

In order to test the effect of various CDs on the aqueous solubility of compound IVQ, 1 mL of each of the following aqueous solutions as described in Table 5 was prepared. Excess IVQ was added to each of these solutions and the samples were shaken at room temperature for 24 hours on an orbital shaker at 200 rpm. Excess IVQ was present in all samples at all times. After 24-hours, the samples were centrifuged. An aliquot of the supernatant was diluted, if necessary, and assayed by HPLC. Table 5 shows that both ACD and HPGCD do not improve aqueous solubility of compound IVQ significantly, while MBCD, SBEBCD, and HPBCD can significantly enhance the aqueous solubility of compound IVQ. These results indicate that only beta cyclodextrins may improve the solubility of compound IVQ. The size of the compound may allow it to form an inclusion body complex, resulting in a higher aqueous solubility. The enhancement effect on the aqueous solubility of compound IVQ is in the order of MBCD>SBEBCD>HPBCD>HPGCD>ACD. MBCD is the most effective solubility improving agent in this experiment.

TABLE 5

Solubility of compound IVQ in different CD's solution

| CD Concentration | Concentration of IVQ (mg/mL) | | | | ACD Concentration | ACD |
|---|---|---|---|---|---|---|
| | HPBCD | MBCD | HPGCD | SBEBCD | | |
| 0 mg/ml | 0.138 | 0.138 | 0.138 | 0.138 | 0 mg/ml | 0.138 |
| 100 mg/ml | 1.215 | 5.776 | N.D. | 0.641 | 40 mg/ml | 0.111 |

Figure 2:
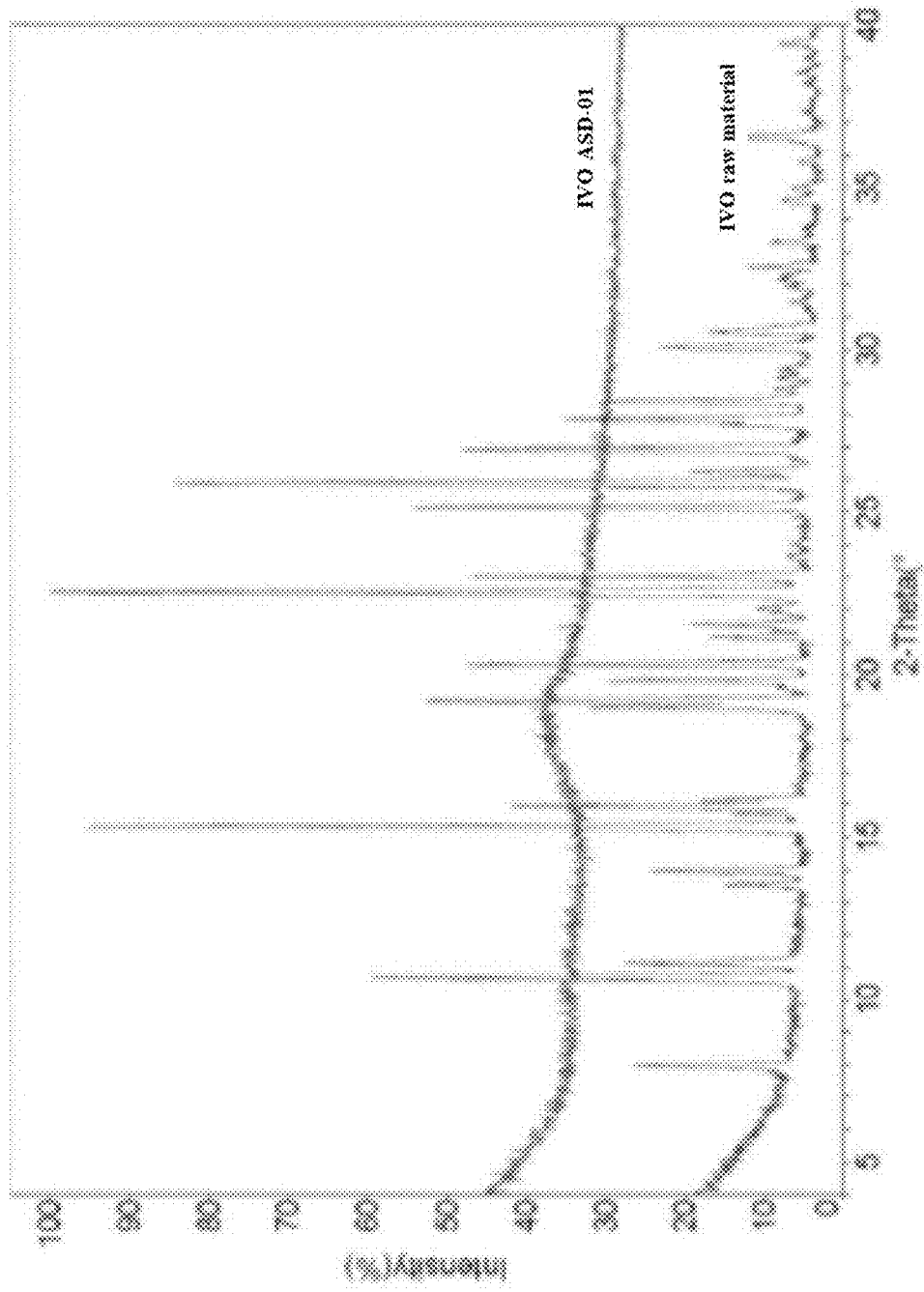
FIG. 2 X-ray powder diffraction (XRPD) results of raw materials and the prepared complex of compound IVO: HPBCD (1:3, w/w) by spray drying method.

Example 6: Preparation of the Complex of Compound IVO with HPBCD by Solvent Evaporation Method Approximate 10.0 g of compound IVO was weighed out into a volumetric flask and completely dissolved in 660 mL of methanol (MeOH) by using ultrasonication (15.2 mg/mL) to get a clear solution. After filtering it with 0.45 um filter membrane to remove potential leftover crystal solid, approximate 30.05 g of HPBCD (Ashland) were added into the solution at a ratio of 25:75 (w/w) of IVO:HPBCD. The sample was stirred for 60 min to form a clear solution before it was spray dried to obtain a solid dispersion. The sample obtained by spray drying was further dried under vacuum condition at 30° C. for 24 hrs. Based on Polarized Light Microscopy (PLM) (FIG. 1) and X-ray powder diffraction (XRPD) (FIG. 2) results, the prepared complex of compound IVO:HPBCD (1:3, w/w) by spray drying method was amorphous, and named as compound IVO/HPBCD ASD-01. FIG. 1 (left) shows that IVO alone is birefringent indicating that IVO is in crystal form. FIG. 1 (right) shows that the IVO/HPBCD complex does not exhibit any birefringence. FIG. 2 shows that the IVO/HPBCD complex does not exhibit any crystal diffraction signals. The IVO/HPBCD is most likely in the form of an inclusion complex, i.e., at least a moiety of the compound of the formula (I) has inserted itself, at least partially, into the cavity of the cyclodextrin. The formation of an inclusion complex changes IVO from crystal form to amorphous status.

TABLE 6

The details of the IVO/HPBCD ASD-01

| Name | ASD |
|---|---|
| Formula | IVO: HPBCD = 25:75 (w/w) |
| Weight | 35 g white solid powder |
| Yield (%) | 87.5 |

TABLE 7

The spray drying parameter setting and results

| Parameters setting | Actual data |
| --- | --- |
| Ratio (IVO: polymer, w/w) | IVO: HPBCD: = 25:75 |
| Nozzle orifice size (mm) | 0.6 |
| Set air speed (m³/min) | 0.40 |
| Actual air speed (m³/min) | 0.40 |
| Set inlet Temp. (° C.) | 80 |
| Actual air Temp. (° C.) | 79.4 |
| Chamber out Temp. (° C.) | 57.4 |
| Cyclone in Temp. (° C.) | 45.9 |
| Upper chamber (mBar) | 3.7 |
| Cyclone pressure (mBar) | 20.5 |
| Set Nozzle airflow (L/min) | 6.8 |
| Actual nozzle airflow (L/min) | 7.6 |
| Cyclone size | medium |
| Cooling air flow (m³/min) | 0.1 |

Example 7: Comparable Solubility Test for IVO ASD-01

Excess IVO, 450 mg HPBCD, 150 mg IVO+450 mg HPBCD physical mixture and 600 mg ASD-1 were prepared in 1.5 ml DI water, then those samples were shaken at room temperature for 24 hours on an orbital shaker at 200 rpm. The samples were centrifuged at 3 and 24 hours. An aliquot of the supernatant was diluted, if necessary, and assayed by HPLC. With same testing condition, IVO ASD-01 showed much higher solubility in water than physical mixture (Table 8).

TABLE 8

Result of comparable solubility test

| Composition | 3 hrs solubility (mg/ml) | 24 hrs solubility (mg/ml) | pH at 24 hrs equilibrium |
| --- | --- | --- | --- |
| 450 mg HPBCD | — | — | 7.06 |
| Excess compound IVO | 0.002 | 0.011 | 8.09 |
| 150 mg compound IVO + 450 mg HPBCD Physical Mixture | 2.400 | 2.207 | 6.88 |
| 600 mg compound IVO ASD-01 | 20.734 | 21.621 | 5.72 |

Example 8: Effect of Additional Excipient on the Solubility of IVO

This study was to explore if there is any synergistic effect by adding additional excipients. As described in Table 9, each of the following aqueous solutions was prepared containing 0; 0.125% 0.25%; 0.5%; 0.75%, 1.5% and 2% additional excipient in 1 mL 30 mg/ml MBCD aqueous solution. An excess of compound IVO was added to each of these solutions and the samples were shaken for 24 hours on an orbital shaker at 200 rpm and at room temperature. Excess of compound IVO was present in all samples at all times. After 24-hours, the samples were centrifuged. An aliquot of the supernatant was diluted, if necessary, and assayed by HPLC. As shown in Table 9, only L-Arginine (L-ARG) shows significant solubility improvement of IVO in 30 mg/ml MBCD solution. The solubility of IVO decreases with the increase of the concentration of citric acid and PEG-400, while no effect was observed for PVP K40, PVP K10, NaCMC, and D-mannitol.

TABLE 9

Excipient effect on the solubility of compound IVO in 30 mg/ml MBCD solution

| Excipient Concentration (w/v) | Solubility of compound IVO (mg/mL) | | | | | | |
| --- | --- | --- | --- | --- | --- | --- | --- |
| | Citric Acid | PEG-4000 | PVP K40 | PVP K10 | NaCMC | L-ARG | D-Mannitiol |
| 0% | 0.18 | 0.18 | 0.18 | 0.18 | 0.16 | 0.18 | 0.18 |
| 0.125% | — | — | 0.20 | 0.18 | 0.17 | 0.70 | 0.20 |
| 0.25% | 0.15 | 0.16 | 0.19 | 0.18 | 0.17 | 0.93 | 0.18 |
| 0.50% | 0.13 | 0.15 | 0.18 | 0.18 | 0.16 | 1.24 | 0.18 |
| 0.75% | 0.09 | 0.17 | 0.18 | 0.18 | 0.16 | 1.60 | 0.19 |
| 1% | 0.09 | 0.15 | 0.19 | 0.18 | 0.16 | 1.83 | 0.19 |
| 1.50% | 0.07 | 0.15 | 0.19 | 0.18 | 0.18 | 2.06 | 0.18 |
| 2% | 0.01 | 0.01 | 0.19 | 0.17 | 0.19 | 2.33 | 0.19 |

Example 9: Effect of L-Arginine on the Aqueous Solubility of Compound IVO 1 mL of each of the following aqueous solutions was prepared containing 0.15% to 2.5% L-ARG in DI water by weight. Excess compound IVO was added to each of these solutions and the samples were shaken at room temperature for 24 hours on an orbital shaker at 200 rpm. Excess compound IVO was present in all samples at all times. After 24-hours, the samples were centrifuged. An aliquot of the supernatant was diluted, if necessary, and assayed by HPLC. Table 10 shows that L-ARG only can improve compound IVO aqueous solubility slightly, much less than that observed in Example 8. This indicates that there is a synergistic effect by combining MBCD and L-Arginine. One possibility is that L-Arginine may help promote the formation of inclusion complex between IVO and MBCD.

TABLE 10

Solubility of compound IVO in solutions containing L-Arginine

| L-Arginine (% w/w) | Compound IVO (ug/ml) |
|---|---|
| 0 | 1.146 |
| 0.15 | 11.07 |
| 0.31 | 15.10 |
| 0.5 | 25.33 |
| 0.63 | 34.20 |
| 1.25 | 46.79 |
| 2.5 | 85.84 |

Figure 3:
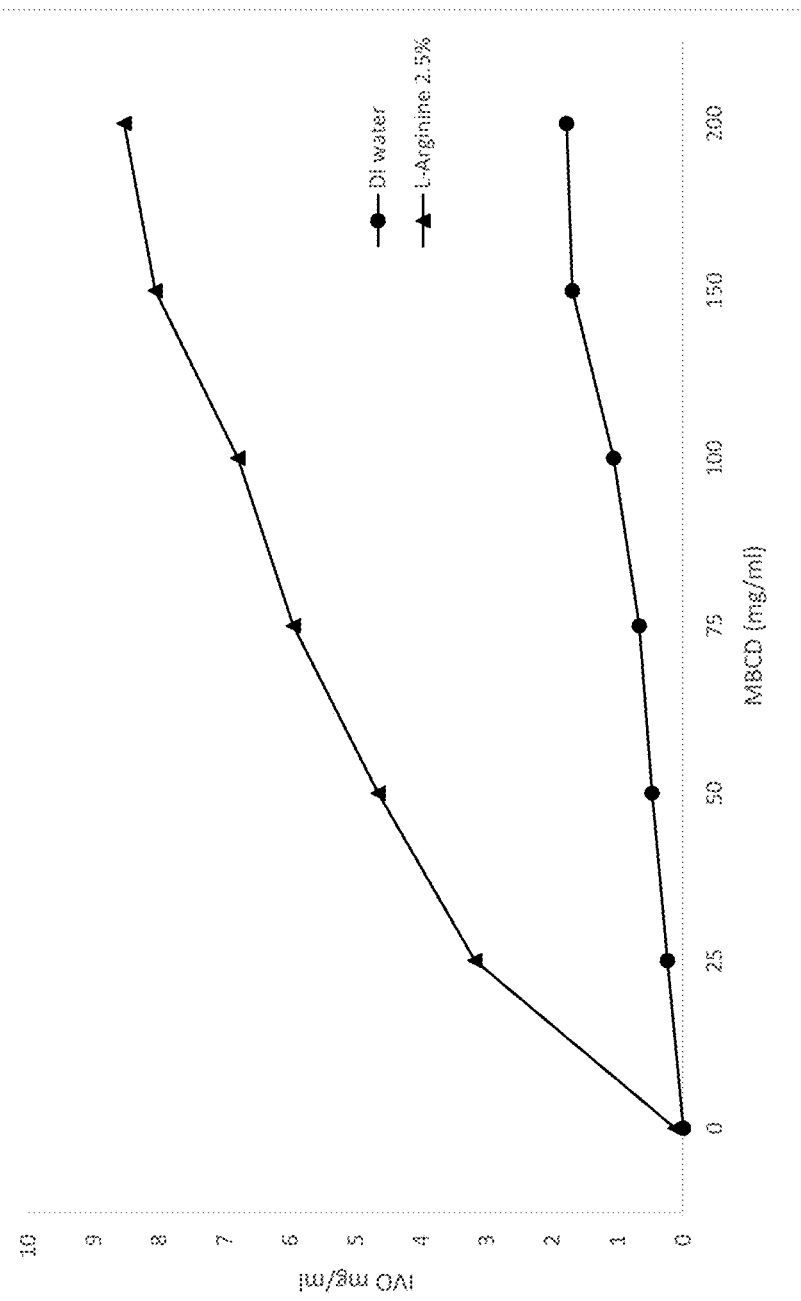
FIG. 3 Effect of MBCD on the solubility of IVO in 2.5% L-ARG solution.
Figure 4:
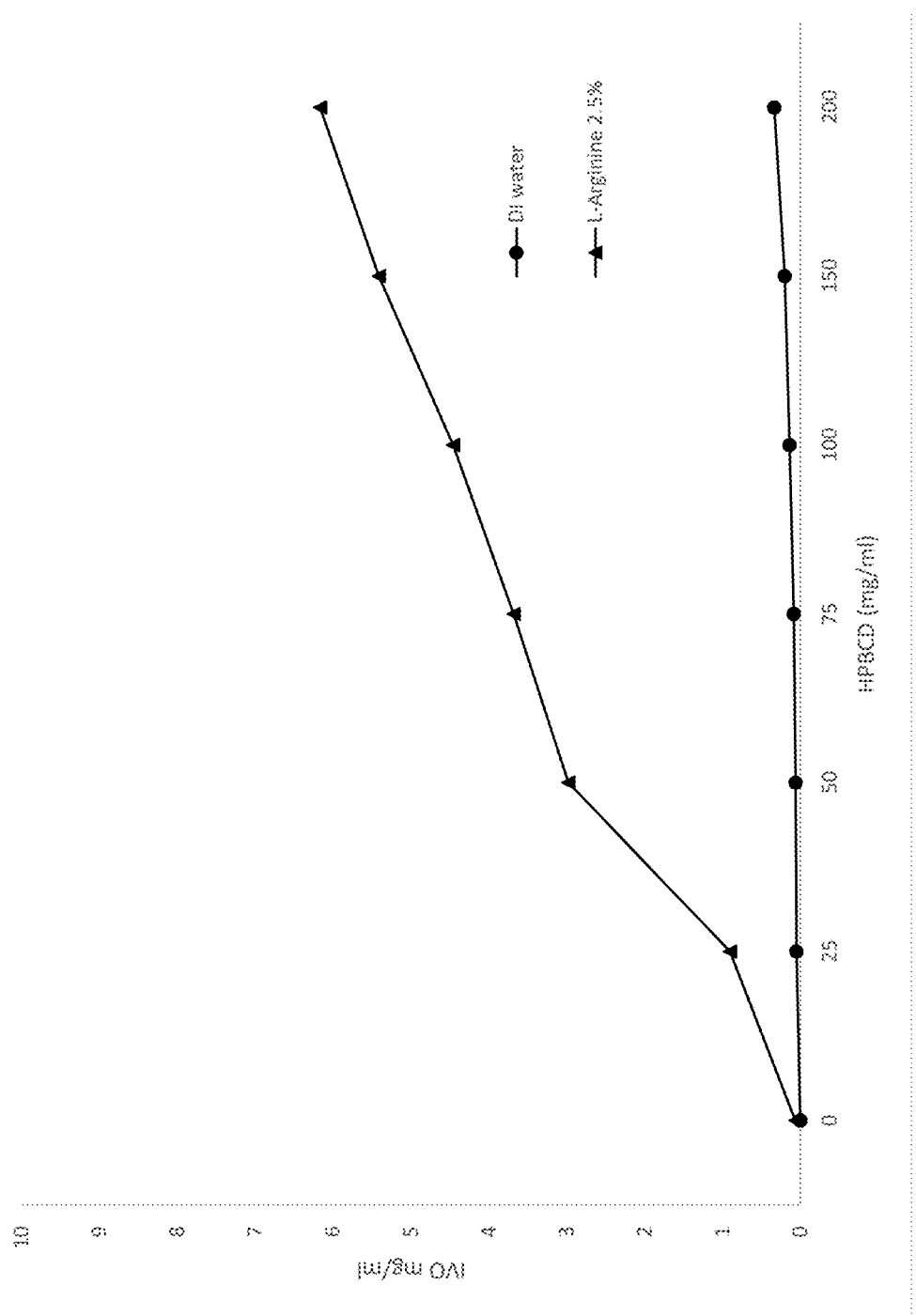
FIG. 4 Effect of HPBCD on the solubility of IVO in 2.5% L-ARG solution.
Figure 5:
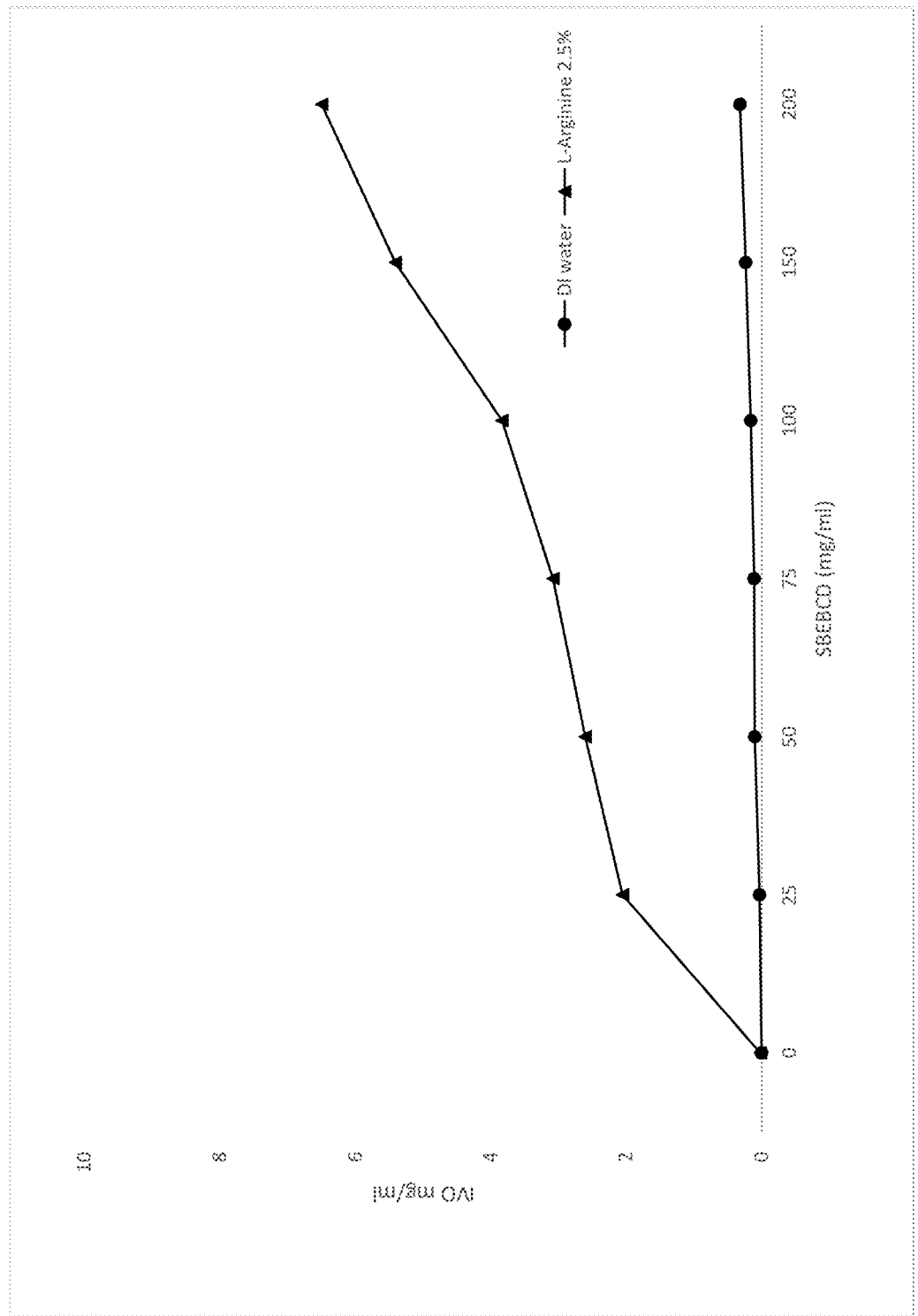
FIG. 5 Effect of SBECD on the solubility of IVO in 2.5% L-ARG solution.

Example 10: Effect of CDs on the Solubility of Compound IVO in 2.5% L-ARG Solution 1 mL of each of the following aqueous solutions was prepared containing 0; 25; 50; 75; 100; 150 and 200 mg/mL CD in 2.5% L-ARG solution. An excess of compound IVO was added to each of these solutions and the samples were shaken at room temperature for 24 hours on an orbital shaker at 200 rpm. Excess compound IVO was present in all samples at all times. After 24-hours, the samples were centrifuged. An aliquot of the supernatant was, if necessary, diluted and assayed by HPLC. FIGS. 3, 4, and 5 shows that L-ARG exhibits syngeneic effect on solubility improvement with all 3 β-CD derivatives. The addition of L-Arginine enhanced the solubility of IVO in MBCD, HPBCD, and SBEBCD aqueous solution for more than 5, 18, and 20 folds, respectively.

Example 11: A Pharmacokinetic Study of IVO Formulations in Beagle Dogs

Introduction

This example describes the pharmacokinetics (PK) of IVO after single oral administration or intravenous injection of different formulations containing IVO to male Beagle dogs.

Materials

Test Animals: Species: Dog; Strain: Beagle; Sex: male; Total Number: A total of 3 males were selected for the study; Body Weight: 8 to 13 kg; Supplier: Marshalls BioResources (New York, N.Y., USA) All in-life records are kept at CTPS, QPS Taiwan.

Study Materials

Nonmicronized IVO Suspension

Nonmicronized IVO (PT-C12071028-F13001) was administered to animals via oral administration as a suspension. The suspension was prepared in 10% (w/v) hydroxypropyl-β-cyclodextrin (HPBCD). A dose of 20 mg/kg was used for the $1^{st}$ dosing group.

Micronized IVO Suspension

Micronized IVO (D-1405FP1321-01) was administered to animals via oral administration as a suspension. The suspension was prepared in 10% (w/v) HPBCD. A dose of 20 mg/kg was used for the $2^{nd}$ dosing group.

Nonmicronized IVO in Capsule

Nonmicronized IVO (PT-C12071028-F13001) was administered to animals via oral administration as a capsule. Capsules were filled in gelatin capsules at testing facility on each dosing day. A dose of 20 mg/kg was used for the $3^{rd}$ dosing group.

Micronized IVO in Capsule

Micronized IVO (D-1405FP1321-01) was administered to animals via oral administration as a capsule. Capsules were filled in gelatin capsules at testing facility on each dosing day. A dose of 20 mg/kg was used for the $4^{th}$ dosing group.

IV of Nonmicronized IVO

Nonmicronized IVO (PT-C12071028-F13001) was dissolved in DMSO and administered to animals via IV injection. A dose of 4 mg/kg was used for the $5^{th}$ dosing group Methods Study Design Dosing and Blood Collection This study was designed in a crossover fashion. Three male dogs consecutively received single dose of Nonmicronized IVO Suspension (20 mg/kg IVO, $1^{st}$ dosing), one dose of Micronized IVO Suspension (20 mg/kg IVO, $2^{nd}$ dosing), one dose of Nonmicronized IVO in Capsule (20 mg/kg IVO, $3^{rd}$ dosing), one dose of Micronized IVO in Capsule (20 mg/kg IVO, $4^{th}$ dosing) and one dose of IV of Nonmicronized IVO (4 mg/kg IVO, $5^{th}$ dosing) with a washout period 3 days) between each treatment in this pharmacokinetic study. Blood was collected from the male dogs pre-dose and at 0.25, 0.5, 1, 2, 4, 6, 8, 12 and 24 h post-dose from the animals in the $1^{st}$ dosing group, the $2^{nd}$ dosing group, the $3^{rd}$ dosing group and the $4^{th}$ dosing group, and pre-dose and at 5 min post-dose and 0.25, 0.5, 1, 2, 4, 6, 8, 12 and 24 h post-dose from the animals in the $5^{th}$ dosing group into tubes containing $K_2EDTA$ as anticoagulant. Blood samples were placed on ice immediately and centrifuged (1500×g for 10 minutes at 4° C.) within 60 minutes of blood collection. Plasma samples were stored at −60° C. or below at CTPS, QPS Taiwan until transferred to QPS Taiwan. A summary of dosing and blood collection times is shown in Table 11.

TABLE 11

Dosing and Blood Collection

| Dosing Day | Treatment Type | No. of Male Animals[a,b] | Route | Dose (mg/kg) | Blood Collection Times[c] |
|---|---|---|---|---|---|
| 1 | Nonmicronized IVO Suspension | 3 | PO | 20 | Pre-dose, 0.25, 0.5, 1, 2, 4, 6, 8, 12 and 24 h post-dose |
| 5 | Micronized IVO Suspension | 3 | PO | 20 | |
| 11 | Nonmicronized IVO in Capsule | 3 | PO | 20 | |
| 15 | Micronized IVO in Capsule | 3 | PO | 20 | |
| 20 | IV of Nonmicronized IVO | 3 | IV | 4 | Pre-dose, 5 min post-dose and 0.25, 0.5, 1, 2, 4, 6, 8, 12 and 24 h post-dose |

[a]The same dogs were administered with different treatments in a crossover fashion with a washout period of more than 3 days between each dosing.
[b]The animal IDs are 13M00001, 13M00007 and 13M00012.
[c]Anticoagulant was K2EDTA.

Plasma Bioanalytical Method

The plasma samples were analyzed at QPS Taiwan using a validated LC-MS/MS method with an LLOQ of 5.000 ng/mL for IVO. Plasma concentrations below the lowest standard were reported as below quantifiable limit (BQL).

Data Analyses

PK Parameters

PK parameters were determined at QPS Taiwan using non-compartmental analysis on individual profile using Phoenix® WinNonlin® 6.3 (Pharsight Corporation, Mountain View, Calif., USA). The observed maximum plasma concentration ($C_{max}$) and the time of $C_{max}$ ($T_{max}$) were determined directly from the data. The area under the plasma concentration-time curve from time-0 to 24 hour post-dose ($AUC_{0-24\ h}$) and the area under the plasma concentration-time curve from time-0 extrapolated to infinity ($AUC_{0-\infty}$) were determined by the linear trapezoidal rule:

$$AUC_{0-24\ h} = (t_2 - t_1) \times (C_1 + C_2)/2$$

with extrapolation to infinity using:

$$AUC_{0-\infty} = AUC_{last} + C_{last}/\lambda$$

Where possible, the apparent terminal elimination half-life ($t_{1/2}$) was calculated according to the following formula, where $\lambda$ is the terminal elimination rate constant:

$$t_{1/2} = \ln(2)/\lambda$$

The selection criteria for inclusion of data points in the calculation of $\lambda$ required that at least three data points representing the terminal phase were regressed and that $r^2 \geq 0.85$ when rounded. Half-life was defined as not determined (ND) if these criteria were not met. Total clearance (CL), mean residence time extrapolated to infinity ($MRT_{0-\infty}$), volume of distribution ($V_z$) and oral bioavailability (F) were determined according to the following formulae:

$$CL = Dose/AUC_{0-\infty,IV}$$

$$MRT_{0-\infty} = AUMC_{0-\infty}/AUC_{0-\infty}$$

$$V_z = Dose/(\lambda \cdot AUC_{0-\infty})$$

$$F = (AUC_{0-\infty,po}/Dose_{po})/(AUC_{0-\infty,IV}/Dose_{IV})$$

Nominal sample collection times were used for AUC, CL and $tv_{1/2}$ calculations. Nominal doses were used for dose normalized $AUC_{0-\infty}$ in all test article-treated groups.

Data Reporting Conventions
Plasma PK Data Analyses
Individual or mean plasma concentrations were reported to three decimal places. Mean plasma concentrations were calculated using SAS® and reported to three decimal places. Individual concentrations that were BQL were set to zero for the calculation of PK parameters.

Individual plasma concentrations were input to WinNonlin™ using values to three decimal places. PK parameters with values up to 999 were reported to three significant figures and values 1000 were reported as whole numbers, with the following exceptions:

$T_{max}$ values are reported to one decimal place if the value is one hour or greater, and to two decimal places if the value is less than one hour.

$\lambda$ values are reported to three decimal places.

CV % values are reported to one decimal place.

Rounding

The computer-generated data shown in the tables have been rounded appropriately for inclusion in this example. As a result, calculation of values from data in this example, in some instances, yields minor variations.

Results And Discussion

The dosing groups and the blood collection schedule for this study are summarized in Table 11. PK parameters for all IVO-treated groups are tabulated in Table 12.

TABLE 12

PK Parameters of IVO in Male Dogs Following Single Oral Administration or IV Injection of Different IVO Formulations
IVO Plasma Pharmacokinetic Parameters (N = 3)

| | Nonmicronized IVO Suspension (20 mg/kg) | | Micronized IVO Suspension (20 mg/kg) | | Nonmicronized IVO in Capsule (20 mg/kg) | | Micronized IVO in Capsule (20 mg/kg) | | IV of Nonmicronized IVO (4 mg/kg) | |
|---|---|---|---|---|---|---|---|---|---|---|
| | Mean | SD | Mean | SD | Mean | SD | Mean | SD | Mean | SD |
| $T_{max}{}^a$ (h) | 4.0 (2.0-4.0) | | 4.0 (2.0-4.0) | | 4.0 (4.0-4.0) | | 1.0 (0.50-2.0) | | 0.08 (0.08-0.08) | |
| $C_{max}$ (ng/mL) | 1037 | 198 | 2524 | 223 | 200 | 147 | 272 | 35.9 | 6818 | 1362 |
| $AUC_{0-24h}$ (h · ng/mL) | 13105 | 3227 | 29085 | 4014 | 1807 | 1648 | 1922 | 130 | 26959 | 5191 |
| $AUC_{0-\infty}$ (h · ng/mL) | 15876 | 6692 | 35021 | 9135 | 1808 | 1696 | 1993 | 200 | 27856 | 5988 |
| $\lambda z$ (1/h) | 0.118 | 0.064 | 0.095 | 0.040 | 0.215 | 0.026 | 0.149 | 0.033 | 0.152 | 0.029 |
| $t_{1/2}$ (h) | 7.6 | 5.1 | 8.2 | 3.3 | 3.3 | 0.4 | 4.8 | 1.2 | 4.7 | 1.0 |
| $MRT_{0-\infty}$ (h) | — | — | — | — | — | — | — | — | 6.6 | 1.2 |
| Vz (L/kg) | — | — | — | — | — | — | — | — | 0.972 | 0.059 |
| CL (L/h/kg) | — | — | — | — | — | — | — | — | 0.148 | 0.028 |
| F (%)[b] | 11.1 | 2.79 | 25.1 | 4.00 | 1.43 | 1.45 | 1.46 | 0.23 | — | — |

—: Not applicable.
[a]Median (range).
[b]F(%) was calculated as $(AUC_{0-\infty,po}/Dose_{po})/(AUC_{0-\infty,IV}/Dos)$ A total of 3 male Beagle dogs were dosed in a cross-over design with five IVO formulations with at least a 3-day washout period between each dosing according to the protocol. No incident with potentially significant impact on the outcome of the study was observed.

No quantifiable levels of IVO were found in all pre-dose samples. Following oral administration of Nonmicronized IVO Suspension (1st dosing group), Micronized IVO Suspension (2nd dosing group), Nonmicronized IVO in Capsule (3rd dosing group) and Micronized IVO in Capsule (4th dosing group), $C_{max}$ of IVO were observed within 2.0-4.0 h, 2.0-4.0 h, all 4 h and 0.5-2.0 h, respectively. Mean $C_{max}$ values were 1037, 2524, 200 and 272 ng/mL in the 1st, 2nd, 3rd and 4th dosing groups, respectively.

Mean $AUC_{0-24\ h}$ values of IVO were 13105, 29085, 1807 and 1922 h·ng/mL, and mean $AUC_{0-\infty}$ values of IVO were 15876, 35021, 1808 and 1993 after oral administration in the 1st, 2nd, 3rd and 4th dosing groups, respectively. Plasma levels declined with a $t_{1/2}$ of 7.6, 8.2, 3.3 and 4.8 h in the $1^{st}$, $2^{nd}$, $3^{rd}$ and $4^{th}$ dosing groups, respectively (Table 12).

Following IV bolus dosing of Nonmicronized IVO at the dose levels of 4 mg/kg, $C_{max}$ of IVO was observed at the first sampling time, 0.08 h post-dose, and averaged 6818 ng/mL. Mean $AUC_{0-24\,h}$ and $AUC_{0-\infty}$ values of IVO were 26959 and 27856 h·ng/mL, respectively. Plasma levels declined with a $t_{1/2}$ of 4.7 h. Mean systemic clearance was 0.148 L/h/kg and mean Vz was 0.972 L/kg. Mean $MRT_{0-\infty}$ was 6.6 h (Table 12). Following oral administration of Nonmicronized IVO Suspension, Micronized IVO Suspension, Nonmicronized IVO in Capsule and Micronized IVO in Capsule, the oral bioavailability (F) of IVO was 11.1%, 25.1%, 1.43% and 1.46%, respectively.

Conclusions

Animals were dosed with IVO as intravenous or oral formulation by single administration. Study results showed that the absorption rate and drug exposure of IVO in the suspension-treated groups were greater than those in the capsule-treated groups. Following oral administration of Nonmicronized IVO Suspension, Micronized IVO Suspension, Nonmicronized IVO in Capsule and Micronized IVO in Capsule, the oral bioavailability (F) was 11.1%, 25.1%, 1.43% and 1.46%, respectively.

Example 12: A Parallel Relative Oral Bioavailability Study of IVO Oral Formulations Following Single Oral (PO) Administration to Non-Naïve Male Beagle Dogs Objective of the Study The objective of this study was to determine the relative oral bioavailability of two IVO formulations (filled in capsules and dosed at 150 mg/dog) compared to a reference formulation of nonmicronized IVO suspension at 20 mg/kg after single oral administration to non-naïve male beagle dogs. Plasma samples were collected from all animals for up to 24 hours post dose, and concentration of IVO was determined by LC-MS/MS method.

Animal Welfare

All applicable portions of the study conformed to the following regulations and guidelines regarding animal care and welfare:

AAALAC International and NIH guidelines as reported in the "Guide for the Care and Use of Laboratory Animals," National Research Council—ILAR, Revised 2011. People's Republic of China, Ministry of Science & Technology, "Regulations for the Administration of Affairs Concerning Experimental Animals", 1988.

Materials and Methods

Test Article and Reference Standard Information

Test formulations and reference standard powder were supplied by the Sponsor. The details and certificate of analysis (CoA) are listed as below:

| Compound ID | Batch No. | Molecular Weight in Free Form | Molecular Weight in Salt Form | Purity (%) | Storage Conditions |
|---|---|---|---|---|---|
| IVO-d9 (Internal Standard) | QP111102 | 403.50 | 403.50 | >99 | RT |
| IVO (Bio-analytical Standard) | PT-C12071028-F13001 | 394.44 | 394.44 | 98.9 | RT |

| Compound ID | Batch | Molecular Weight in Free Form | Weight in Salt Form | Salt Factor* | Purity (%) |
|---|---|---|---|---|---|
| IVO (Group 1, non-micronized API) | PT-C12071028-F13001 | 394.44 | 394.44 | 1.00 | 98.9 |

| Formulation ID | Batch | Potency (%) (% drug load) | Purity (%) | Correct Factor |
|---|---|---|---|---|
| IVO ASD-01 (Group 2) | YF00892-003-141219-01 | 24.19 | 99.20 | 4.167 |
| IVO granules (Group 3) | YF00892-006-141224-01 | 23.81 | 99.01 | 4.242 |

*Salt Factor = Molecular weight in salt form/Molecular weight in free form
Correct Factor = (Molecular weight in salt form/Molecular weight in free form)/Purity/Potency Test System, Study Design and Animal Care Test System Nine non-naïve male beagle dogs (7.40-9.78 kg) were used in this study. Animals were obtained from an approved vendor (Marshall Bioresources, Beijing, China) and each animal had a unique skin tattoo number on ear as the identification.

Study Design

| Group | # of Males | Animal ID | Test Article | Formulation | Dose Route | Target Dose Level | Target Dose Volume (mL/kg) | Target Dose Concentration (mg/mL) |
|---|---|---|---|---|---|---|---|---|
| 1 | 3 | D101 D102 D103 | IVO suspension | Suspension (reference) Vehicle: 10% (w/v) Hydroxypropyl-β-cyclodextrin (HPBCD) in water for injection | PO | 20 mg/kg | 4.0 | 5.0 |
| 2 | 3 | D201 D202 D203 | IVO ASD-01 | Capsule (test) | PO | 150 mg/dog | NA | NA |
| 3 | 3 | D301 D302 D303 | IVO granules | Capsule (test) | PO | 150 mg/dog | NA | NA |

Animal Care

The animal room was controlled and monitored for humidity (targeted mean range 40% to 70%) and temperature (targeted mean range 18° C. to 26° C.) with 10 to 20 air changes/hour. The room was on a 12-hour light/dark cycle except when interruptions were necessitated by study activities.

Animals were individually housed in stainless-steel mesh cages during in-life that were in accordance with the National Research Council "Guide for the Care and Use of Laboratory Animals".

Animals were fed twice each day. Stock dogs were fed approximately 220 grams of Certified Dog Diet daily (Beijing Vital Keao Feed Co., Ltd. Beijing, P. R. China). These amounts were adjusted as necessary based on food consumption of the group or an individual body weight changes of the group or an individual and/or changes in the certified diet.

For fasted group (PO dose groups) animals were fed the afternoon (at 3:30 to 4:00 pm) prior to the day of oral dosing and the remaining food was removed at about 7:00 pm. Food was withheld until 4-hour post-dose unless specified in this protocol. Fasted animals were fed once on the day of dosing, with the amount of approximately 220 grams.

Animals were provided reverse-osmosis purified and chlorinated water ad libitum by an automated watering system.

Nutritional components and environmental contaminants in the diet were analyzed routinely by the vendor or an independent laboratory, respectively. The analysis reports and lot numbers are on file at the Testing Facility.

The animal drinking water was analyzed for contaminants each quarter by an independent laboratory. Water analysis reports are on file in Veterinary Operation's department at the Testing Facility.

Formulation Preparation

For suspension formulation preparation:

IVO suspension for Group 1 at a concentration of 5 mg/mL in 10% (w/v) Hydroxypropyl-β-cyclodextrin in water for injection was prepared on the dosing day. The detailed information of the vehicle used and the dose formulation preparation procedure were recorded in the study folder.

For capsule formulation preparation:

Gelatin capsules (size: 0#) were used in this study for Groups 2 & 3.
a. Animals were weighed on the dosing day, and the body weight ranging at 10±1 kg were selected, except for 7.91 kg of animal D303 was selected.
b. 150 mg API of the formulation was filled in the capsules.
c. 3 capsules in total were dosed per dog.

Details of capsules weight are presented in Table 13.

TABLE 13

Capsule weights

| Test Article | Drug Route | Group | Animal No. | Capsule Weight (mg) | Total (mg) |
|---|---|---|---|---|---|
| IVO ASD-01 in capsule | PO | 2 | D201 | 212.19<br>202.77<br>210.15 | 625.11 |
| | | | D202 | 211.31<br>204.84<br>208.90 | 625.05 |

TABLE 13-continued

Capsule weights

| Test Article | Drug Route | Group | Animal No. | Capsule Weight (mg) | Total (mg) |
|---|---|---|---|---|---|
| | | | D203 | 209.47<br>208.33<br>207.33 | 625.13 |
| IVO Granules in capsule | | 3 | D301 | 212.09<br>214.13<br>210.17 | 636.39 |
| | | | D302 | 216.87<br>213.64<br>205.79 | 636.30 |
| | | | D303 | 206.79<br>207.84<br>222.88 | 637.51 |

Administration

The IVO formulations were orally administered in accordance with SOPs:

Orally for suspension formulation:

The gavage doses were flushed using 6 mL of vehicle (approximately 3 times volume of gavages tube). All tubes were equal size and cut to equal length so that the flush volume was comparable.

Orally for capsule formulation:
a. Pulled lower jaw of dogs down and placed the capsule far back in the throat. The capsule was then pushed past the pharynx by using a thumb or index finger.
b. To facilitate swallowing of capsule, 6 mL of water was given to the animal following each capsule administration.
c. After administering the capsule, swallowing was induced by gently stroking the dog's throat.
d. After administration, the dog's mouth was inspected to ensure that the capsule had been swallowed.

Animals were weighed prior to each dose administration, and the body weights of the individual animals are presented in Table 14.

TABLE 14

Animal Body Weights

| Test Article | Drug Route | Group | Animal No. | Body Weight (kg) |
|---|---|---|---|---|
| IVO (non-micronized API) | PO | 1 | D101<br>D102<br>D103 | 8.63<br>8.77<br>7.40 |
| IVO ASD-01 in capsule | | 2 | D201<br>D202<br>D203 | 9.35<br>9.08<br>9.78 |
| IVO Granules in capsule | | 3 | D301<br>D302<br>D303 | 9.29<br>9.33<br>7.91 |

Sample Collection and Preparation

Serial blood samples (approximately 0.8 mL in 10 μL 0.5M K2-EDTA) were collected via venipuncture from a cephalic vein from non-sedated animals at pre-dose (0), 0.25 (15 mins), 0.5 (30 mins), 1, 2, 4, 6, 8, 12 and 24 hours post dose. Actual sample collection times were recorded in the study folder. For samples collected within the first hour of dosing, a ±1 minute of the scheduled time was acceptable. For the remaining time points, samples that were taken within 5% of the scheduled time were acceptable and were not considered as protocol deviation.

After collection, blood samples were gently inverted several times and immediately placed on wet ice prior to centrifugation at 2-8° C. and 3000×g for 10 minutes within 1 hour after blood collection. The plasma samples were then transferred into labeled polypropylene micro-centrifuge tubes, snap frozen and transferred to bioanalysis department on dry ice, and stored frozen in a freezer set to maintain −60° C. or lower until bio-analysis.

Clinical Observation

Twice daily (at approximately 9:30 a.m. and 3:30 p.m.), animals were observed for mortality and signs of pain and distress. Cage-side observations for general health and appearance were made once daily. On the dosing day, the animals were observed before and after each blood collection time point. Any unusual observations noted throughout the duration of the study were recorded in the study folder.

Sample Analysis

Plasma samples were analyzed by using a LC/MS-MS method. The lower limit of quantification (LLOQ) for IVO in plasma was 2.00 ng/mL and the upper limit of quantification (ULOQ) was 3000 ng/mL.

Pharmacokinetic Data Analysis

Plasma concentration-time profiles of IVO were subjected to a non-compartmental pharmacokinetic analysis using WinNonlin software program (version 6.2.1).

The mean residence time (MRT), the area under the plasma concentration time curve (AUC) from time zero to the last quantifiable time point (AUC0-last) and AUC from time zero to infinity (AUC0-inf) were calculated using the linear-log trapezoidal rule (See: Gabrielsson J. and Weiner D. Non-compartmental analysis in "Pharmacokinetic and Pharmacodynamic Data Analysis: Concepts & Applications", 3rd edition, Chapter 3.7.2., page 141-146. Swedish Pharmaceutical Press; 2002).

All the values except for time values were reported to three significant figures. Time values were reported to two decimal places.

Nominal sampling times were used to calculate all pharmacokinetic parameters since there was no deviation between the actual and the nominal sampling times.

Results

Clinical Observations

About 10 mL light yellow vomited mucus with empty capsule shell was observed for animal D203 of Group 2 at 1 hour post dose. No abnormal effect was observed for the other study animals during this study.

Dose Concentration Verification

Dose concentration verification of Group 1 showed an accuracy of 101%.

Pharmacokinetics

Pharmacokinetic parameters of IVO are presented in Table 15.

TABLE 15

Pharmacokinetic parameters of IVO formulations

| Formulation | IVO suspension (20 mg/kg) | IVO ASD-01 (Capsule, 150 mg/dog) | IVO Granules (Capsule, 150 mg/dog) |
| --- | --- | --- | --- |
| Dose (mg/kg) | 20.2 | 16.0 | 17.1 |
| $C_{max}$ (ng/mL) | 1453 | 3947 | 1071 |
| $T_{max}$ (h) | 4.00 | 1.67 | 3.33 |
| $AUC_{0-last}$ (ng · h/mL) | 12630 | 20100 | 7077 |
| $AUC_{0-inf}$ (ng · h/mL) | 12963 | 20233 | 6215 |
| $AUC_{0-last}$/Dose (ng · h/mL/(mg/kg)) | 625 | 1249 | 410 |
| $MRT_{0-last}$ (h) | 6.66 | 4.52 | 7.17 |
| $MRT_{0-inf}$ (h) | 7.20 | 4.65 | 5.82 |
| Relative F% (based on $AUC_{0-last}$) | NC | 200 | 65.5 |

Conclusions

Following single oral administration of non-micronized IVO suspension at 20 mg/kg to non-naïve male beagle dogs in fasted state, the maximum plasma concentration (Cmax) was 1453±90.7 ng/mL occurred at 4.00±3.46 hours post dose (Tmax). The plasma exposures, AUC0-inf and AUC0-last were 12963±4191 and 12630±3948 ng·h/mL, respectively.

Following single oral administration of IVO ASD-01 in capsule at 150 mg/dog to non-naïve male beagle dogs in fasted state, the maximum plasma concentration (Cmax) was 3947±1740 ng/mL occurred at 1.67±0.58 hours post dose (Tmax). The plasma exposures, AUC0-inf and AUC0-last were 20233±8545 and 20100±8391 ng·h/mL, respectively.

Following single oral administration of IVO granules in capsule at 150 mg/dog to non-naïve male beagle dogs in fasted state, the maximum plasma concentration (Cmax) was 1071±597 ng/mL occurred at 3.33±2.31 hours post dose (Tmax). The plasma exposures, AUC0-inf and AUC0-last were 6215±NC and 7077±3749 ng·h/mL, respectively.

Compared with the reference formulation, IVO ASD-01 in capsule was absorbed more rapidly (Tmax=1.67), while IVO granules in capsules showed a similar Tmax at 3.33 hours compared to the reference formulation. The systemic exposure (AUC) and maximum plasma concentrations (Cmax) of IVO were much higher for IVO ASD-01 in capsule than those of the reference formulation. The IVO granules in capsule showed a lower oral absorption compared to the reference formulation.

The relative bioavailability of IVO ASD-01 and IVO granules was 200% and 65.5% compared with the reference formulation, respectively.

Example 13: Comparison of IVO/HPBCD ASD-in-Capsule to IVO API-in-Capsule in Beagle Dogs A formulation of nonmicronized IVO oral suspension (20 mg/kg) was used as a reference. The suspension was prepared in 10% (w/v) hydroxypropyl-β-cyclodextrin (HPBCD). A dose of 20 mg/kg was used (IVO Suspension) as shown in Examples 11 and 12.

IVO API-in-Capsule was tested in Example 11 with the reference. IVO:HPBCD complex at a ratio of 25:75 (w/w) was prepared according to the procedure described in Example 6. IVO/HPBCD ASD-in-Capsule was tested in Example 12 along the reference.

Table 16 shows the PK parameters of three different formulations dosed orally in beagle dogs. IVO API is highly crystalline and has very low aqueous solubility. The formulation IVO API-in-Capsule (neat API filled in oral capsules) showed lower AUC and Cmax than that of the reference formulation. In contrast, an improved oral formulation, IVO/HPBCD ASD-in-Capsule, shows significantly increased aqueous solubility. As a result, the oral absorption (AUC) and Cmax of IVO was significantly increased using IVO/HPBCD complex ASD-in-Capsule, by approximately 17-fold and 18-fold, respectively, in dogs when compared to IVO API-in-Capsule, as shown in Table 16.

TABLE 16

PK comparison of IVO/HPBCD ASD-in-Capsule to IVO API-in-Capsule in Beagle Dogs

| Study | Example 11 | | Example 12 | |
|---|---|---|---|---|
| Formulation Description | Test API-in-Capsule | Reference IVO suspension | Test ASD-in-Capsule | Reference IVO suspension |
| Dose (mg/kg) | 20.0 | 20.0 | 16.0 | 20.2 |
| $C_{max}$ (ng/m L) | 200 | 1037 | 3947 | 1453 |
| $T_{max}$ (h) | 4.0 | 4.0 | 1.7 | 4.0 |
| $AUC_{0-inf}$ (h * ng/mL) | 1808 | 15876 | 20233 | 12963 |
| $AUC_{0-inf}$/Dose | 90.4 | 793.8 | 1264.6 | 641.7 |
| $C_{max}$/Dose | 10.0 | 51.9 | 246.7 | 71.9 |
| $AUC_{0-inf}$ Ratio (ASD/API)[a] | 17 | | | |
| $C_{max}$ Ratio (ASD/API)[a] | 18 | | | |

[a] Ratios were calculated after normalization with the parameters of reference formulation.

Compared with the reference formulations, IVO/HPBCD ASD-01 in capsule was absorbed more rapidly (Tmax=1.7), while IVO API-in-Capsule showed a same Tmax at 4 hours in comparison to the reference formulation. Overall, HPBCD can significantly improve the solubility of IVO in water and enhance systemic absorption.

What is claimed is:

1. A pharmaceutical composition comprising a compound of formula (I) or a salt thereof, and a cyclodextrin, wherein R is selected from the group consisting of phenyl, 4-benzyloxyphenyl, 4-biphenyl, 4-methoxyphenyl, 3-methoxyphenyl, 2-methoxyphenyl, 3,5-dimethoxyphenyl, 4-chlorophenyl, 3-chlorophenyl, 2-chlorophenyl, 4-methylphenyl, 3-methylphenyl, 2-methylphenyl, and 3-trifluoromethylphenyl

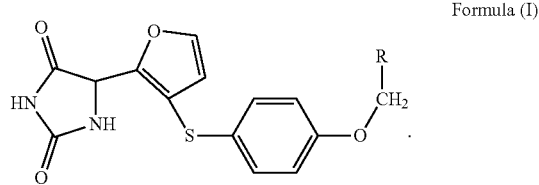

Formula (I)

2. The pharmaceutical composition of claim 1, wherein the molar ratio of the compound of formula (I) to the cyclodextrin is from 1:1 to 1:50.

3. The pharmaceutical composition of claim 1, wherein the cyclodextrin is a beta-cyclodextrin, and the pharmaceutical composition increases the solubility of the compound of formula (I) in deionized water at room temperature, by at least 1.5-fold compared to the solubility of the compound of formula (I) without the cyclodextrin under the same conditions.

4. The pharmaceutical composition of claim 1, wherein the cyclodextrin is a unsubstituted or substituted alpha-cyclodextrin, beta-cyclodextrin, or gamma-cyclodextrin.

5. The pharmaceutical composition of claim 4, wherein the beta-cyclodextrin is selected from the group consisting of a methyl beta-cyclodextrin, a hydroxypropyl beta-cyclodextrin, and a sulfobutylether beta-cyclodextrin.

6. The pharmaceutical composition of claim 1, wherein at least a moiety of the compound of the formula (I) has inserted itself, at least partially, into the cavity of the cyclodextrin.

7. A pharmaceutical composition comprising a compound of the formula (I) or a salt thereof; a cyclodextrin; and an excipient, wherein R is selected from the group consisting of phenyl, 4-benzyloxyphenyl, 4-biphenyl, 4-methoxyphenyl, 3-methoxyphenyl, 2-methoxyphenyl, 3,5-dimethoxyphenyl, 4-chlorophenyl, 3-chlorophenyl, 2-chlorophenyl, 4-methylphenyl, 3-methylphenyl, 2-methylphenyl, and 3-trifluoromethylphenyl

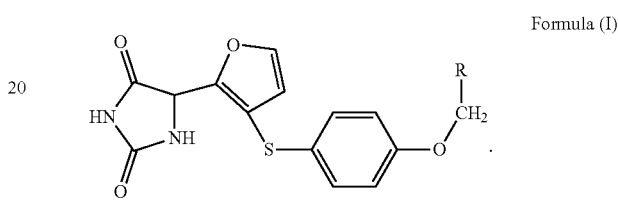

Formula (I)

8. The pharmaceutical composition of claim 7, wherein the molar ratio of the compound of formula (I) to the cyclodextrin is from 1:1 to 1:50.

9. The pharmaceutical composition of claim 7, wherein the cyclodextrin is a beta-cyclodextrin, and the pharmaceutical composition increases the solubility of the compound of formula (I) in deionized water at room temperature, by at least 1.5-fold compared to the solubility of the compound of formula (I) without the cyclodextrin under the same conditions.

10. The pharmaceutical composition of claim 7, wherein the cyclodextrin is a unsubstituted or substituted alpha-cyclodextrin, beta-cyclodextrin, or gamma-cyclodextrin.

11. The pharmaceutical composition of claim 10, wherein the beta-cyclodextrin is selected from the group consisting of a methyl beta-cyclodextrin, a hydroxypropyl beta-cyclodextrin, and a sulfobutylether beta-cyclodextrin.

12. The pharmaceutical composition of claim 7, wherein the excipient is selected from the group consisting of Citric Acid, PEG-4000, PVP K40, PVP K10, NaCMC, and D-Mannitol.

13. The pharmaceutical composition of claim 7, wherein at least a moiety of the compound of the formula (I) has inserted itself, at least partially, into the cavity of the cyclodextrin.

14. The pharmaceutical composition of claim 1, wherein the cyclodextrin is a sulfobutylether beta-cyclodextrin, and the compound of formula (I) is 5-{3-[4-(3-Methyl-benzyloxy) phenylthio]fur-2-yl}imidazolidine-2,4-dione.

15. The pharmaceutical composition of claim 14, wherein the sulfobutylether beta-cyclodextrin is at a concentration of about 10% (w/v), relative the volume of the pharmaceutical composition.

16. The pharmaceutical composition of claim 15, wherein the pharmaceutical composition increases the oral bioavailability of the compound in a mammal by at least 50% over the oral bioavailability of the compound without the cyclodextrin under the same conditions.

17. The pharmaceutical composition of claim 15, wherein the pharmaceutical composition induces at least 2-times greater Cmax of the compound than Cmax of the compound when the compound is administered alone in the same amount and under the same conditions.

18. The pharmaceutical composition of claim 7, wherein the cyclodextrin is a sulfobutylether beta-cyclodextrin, and the compound of formula (I) is 5-{3-[4-(3-Methyl-benzyloxy) phenylthio]fur-2-yl}imidazolidine-2,4-dione.

19. The pharmaceutical composition of claim 18, wherein the sulfobutylether beta-cyclodextrin is at a concentration of about 10% (w/v), relative the volume of the pharmaceutical composition.

20. The pharmaceutical composition of claim 19, wherein the pharmaceutical composition increases the oral bioavailability of the compound in a mammal by at least 50% over the oral bioavailability of the compound without the cyclodextrin under the same conditions.

21. The pharmaceutical composition of claim 19, wherein the pharmaceutical composition induces at least 2-times greater Cmax of the compound than Cmax of the compound when the compound is administered alone in the same amount and under the same conditions.

\* \* \* \* \*